(12) United States Patent
Li

(10) Patent No.: US 6,687,327 B2
(45) Date of Patent: Feb. 3, 2004

(54) SYSTEM AND METHOD OF MEDICAL IMAGING HAVING TASK AND/OR PATIENT SIZE DEPENDENT PROCESSING

(75) Inventor: Jianying Li, New Berlin, WI (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 131 days.

(21) Appl. No.: 09/683,073

(22) Filed: Nov. 15, 2001

(65) Prior Publication Data

US 2003/0091142 A1 May 15, 2003

(51) Int. Cl.[7] .................................................. H05G 1/60
(52) U.S. Cl. .................................................. 378/8; 378/4
(58) Field of Search .......................... 378/8, 4, 19, 98.8, 378/18, 210

(56) References Cited

U.S. PATENT DOCUMENTS

| | | | | |
|---|---|---|---|---|
| 5,225,980 A | * | 7/1993 | Hsieh et al. ............ | 364/413.14 |
| 5,552,602 A | * | 9/1996 | Kakibayashi et al. ........ | 250/311 |
| 5,694,449 A | * | 12/1997 | Aragones ..................... | 378/115 |
| 6,233,310 B1 | * | 5/2001 | Reliham et al. ............ | 378/108 |
| 6,236,705 B1 | | 5/2001 | Stergiopoulos et al. | |
| 6,295,331 B1 | | 9/2001 | Hsieh | |
| 6,449,330 B1 | * | 9/2002 | Li et al. ......................... | 378/4 |
| 6,459,765 B1 | * | 10/2002 | Ganin et al. ................ | 378/108 |
| 6,553,095 B2 | * | 4/2003 | Rinaldi et al. .............. | 378/108 |

* cited by examiner

*Primary Examiner*—Craig E. Church
*Assistant Examiner*—Irakli Kiknadze
(74) *Attorney, Agent, or Firm*—Ziolkowski Patent Solutions Group, LLC; Michael A. Della Penna; Carl B. Horton

(57) ABSTRACT

A system and method of medical imaging is designed to reduce a patient's X-ray exposure during scanning based upon patient size and task dependency. The system includes receiving a task and patient size dependency input and determining threshold levels based on the received inputs to separate imaging data into a number of projection sets for further image processing and reconstruction of an image. Each projection set can then be independently processed based on the type of task and/or the patient size to allow reduced and modified X-ray doses dependent on the task and/or specific patient to be scanned.

30 Claims, 2 Drawing Sheets

SYSTEM AND METHOD OF MEDICAL IMAGING HAVING TASK AND/OR PATIENT SIZE DEPENDENT PROCESSING

BACKGROUND OF THE INVENTION

The present invention relates generally to medical imaging and, more particularly, to a system and method of imaging a region of interest (ROI) based upon patient size and/or task selection, preferably in computed tomography systems.

Typically, in computed tomography (CT) imaging systems, an X-ray source emits a fan-shaped beam toward an object, such as a patient. The beam, after being attenuated by the patient, impinges upon an array of radiation detectors. The intensity of the attenuated beam radiation received at the detector array is typically dependent upon the attenuation of the X-ray beam by the patient. Each detector element of the detector array produces a separate electrical signal indicative of the attenuated beam received by each detector element. The electrical signals are transmitted to a data processing unit for analysis which ultimately results in the formation of an image.

Generally, the X-ray source and the detector array are rotated with a gantry within an imaging plane and around the patient. X-ray sources typically include X-ray tubes, which conduct a tube current and emit the X-ray beam at a focal point. X-ray detectors typically include a collimator for collimating X-ray beams received at the detector, a scintillator for converting X-rays to light energy adjacent the collimator, and photodiodes for receiving the light energy from the adjacent scintillator.

In one known CT imaging system used to image an ROI, imaging of a patient is conducted by moving the patient through a gantry. Preferably, it is desirable to minimize the patient's exposure to X-rays. To do so, improved signal processing has allowed the use of lower dose CT scans, such as the commercially available 0.5 second CT scanner. However, for larger and heavier patients, low signal streaking problems are known to occur due to low tube current values for certain angular views. One proposed solution to the low signal streaking problem is to determine a threshold based upon clinical evaluation of large or heavy patient scans. The determined threshold is then fixed, and corrections during image processing are performed based upon a signal strength that corresponds to X-rays being attenuated by large or dense objects. Problems arise, however, when reducing the dose in CT scans further, and in particular, for smaller patients and task dependent scans.

There is a need for a system that can apply the lowest possible patient doses based on patient size, especially for pediatric patients, and/or based on a task to be performed. Setting fixed patient thresholds to correct for low signal streaking problems in medium and smaller size patients does not improve reconstructed images of the patients, but may expose such patients to unnecessary X-ray radiation. Furthermore, certain sub-regions of the ROI may require a lower image resolution, or alternatively, a particular task such as Cardiac Artery Calcification Scoring may require a lower image resolution as compared to Cardiac Artery imaging thereby permitting application of a lower patient dose of radiation.

Since lower radiation exposure is an on-going goal in X-ray and CT development, it would be desirable to have an imaging system capable of processing imaging data according to an automated selection of a patient size and/or task dependency to reduce a patient's X-ray exposure during scanning of the patient.

BRIEF DESCRIPTION OF THE INVENTION

The present invention provides a system capable of processing imaging data according to selection of a patient size and/or task dependency to reduce a patient's X-ray exposure during scanning of the patient, and a method of processing imaging data that solves the aforementioned drawbacks.

A system and method of computer tomography imaging to reduce a patient's X-ray exposure based upon patient size and/or task selection prior to scanning of the patient are provided. The system includes a high frequency electromagnetic energy projection source to project X-rays towards an object, such as a patient. A detector receives the high frequency energy attenuated by the patient, and a plurality of electrical interconnects is configured to transmit detector outputs to a data processing system. The system also includes a computer capable of receiving a task and patient size dependency selection input and determining a threshold level based on the received inputs to separate the detector outputs into a number of projection sets for further image processing to reconstruct an image.

In accordance with one aspect of the present invention, a method of processing imaging data for a radiation emitting medical device includes the steps of providing a task and patient size dependency selection and setting a first threshold level based on the task and patient size dependency selection. The method also includes the steps of acquiring imaging data and separating the imaging data into a plurality of projection sets based on the first threshold level. The method further includes the step of uniquely processing the imaging data of each projection set to reconstruct an image.

In accordance with another aspect of the invention, a computed tomography system is provided. This system includes a high frequency electromagnetic energy projection source to project high frequency energy towards an object and a detector to receive high frequency electromagnetic energy attenuated by the object. The detector produces outputs that are transmitted to a data processing system by a plurality of electrical interconnects. The system further includes a computer programmed to receive the detector outputs and a task and patient size selection input, and determine threshold levels based on the received task and patient size selection input. The computer is further programmed to separate the detector outputs into a plurality of projection sets based on the threshold levels, and reconstruct the separated plurality of projection sets to produce a visual image.

In accordance with yet another aspect of the invention, a computer-readable medium having stored thereon a computer program having a set of instructions that, when executed by a computer, will cause the computer to receive a selection signal of a task and patient size input, and determine at least one threshold based upon the received selection signal. The computer program also has instructions to receive imaging data signals acquired with low-dose radiation, and synthesize the imaging data signals into a plurality of projection sets. The computer further includes instructions to process each projection set based on the selection signal and the threshold, and to reconstruct a visual image with improved artifact reduction.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

A system and method is described for a computed tomography (CT) system capable of imaging an ROI. It will be appreciated by those of ordinary skill in the art that the present invention is equally applicable for use with different CT system configurations. Moreover, the present invention will be described with respect to the detection and conversion of X-rays. However, one of ordinary skill in the art will further appreciate, that the present invention is equally applicable in other imaging modalities.

Figure 1:
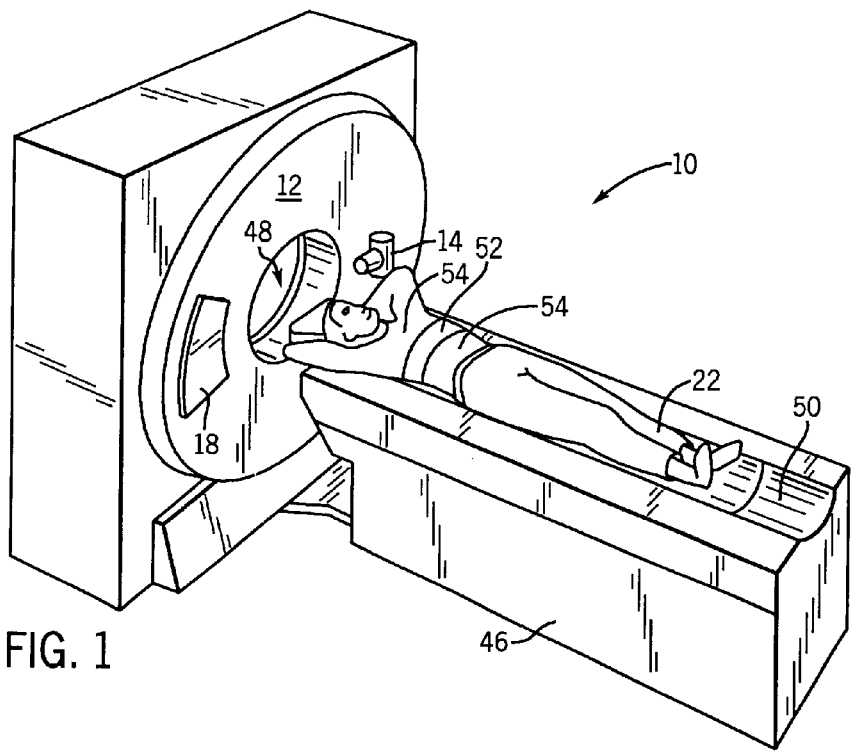
FIG. 1 is a perspective view of a CT imaging system incorporating the present invention.
Figure 2:
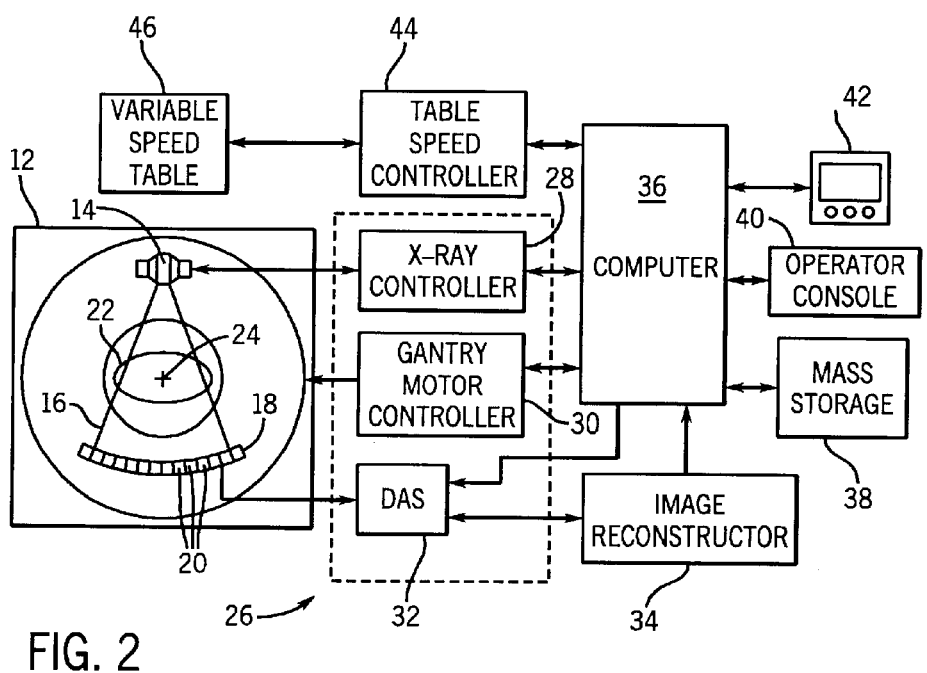
FIG. 2 is a perspective block schematic diagram of the system illustrated in FIG. 1.

Referring to FIGS. 1 and 2, an exemplary computed tomography (CT) imaging system 10 is shown as including a gantry 12 representative of a "third generation" CT scanner. Gantry 12 has an X-ray source 14 that projects a beam of X-rays 16 toward a detector array 18 on the opposite side of the gantry 12. Detector array 18 is formed by a plurality of detectors 20 which together sense the projected X-rays that pass through a medical patient 22. Each detector 20 produces an electrical signal that represents the intensity of an impinging X-ray beam and hence the attenuated beam as it passes through the patient 22. During a scan to acquire X-ray projection data, gantry 12 and the components mounted thereon rotate about a center of rotation 24. Detector array 18 and detectors 20 can be any number of high frequency electromagnetic energy detectors, such as gas-filled, scintillation cell-photodiode, and semiconductor detectors as is know to those skilled in the art of detector design.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized X-ray data from DAS 32 and performs high-speed reconstruction. The reconstructed image is applied as an input to a computer 36 which stores the image in a mass storage device 38.

Computer 36 also receives commands and scanning parameters, such as patient size and task dependency, from an operator via console 40 that has a keyboard for entering commands and scanning parameters. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table speed controller 44 which controls a variable speed table 46 during imaging of a patient 22 within gantry 12. Particularly, table 46 is configured to move a patient 22 through a gantry opening 48 along an axis 50, and may include a single or multiple speed settings.

In operation, a patient 22 or object is positioned within the CT scanner or imaging device 10 on the variable speed table 46 with a selected region of the patient chosen for scanning adjacent to the gantry 12. A technician or health-care operator enters input into the operator console 40, thereby defining a ROI or scanning region such as a thorax of the patient 22, which includes a cardiac region 52 and a pair of non-cardiac regions 54. The computer 36 then instructs the table speed controller 44 to move the table 46 towards the gantry opening 48 causing the patient 22 to enter the gantry opening 48. Control mechanism 26 causes X-ray controller 28 to provide power and timing signals to X-ray source 14 while the gantry motor controller 30 causes rotation of gantry 12 to conduct an imaging scan of the patient 22 passing through the gantry 12.

After scanning the ROI, detectors 20 send the X-ray data acquired to DAS 32 and image reconstructor 34 for digitalization and image reconstruction. Computer 36 then processes the digitized X-ray data to provide a reconstructed image of the ROI on display 42.

Figure 3:
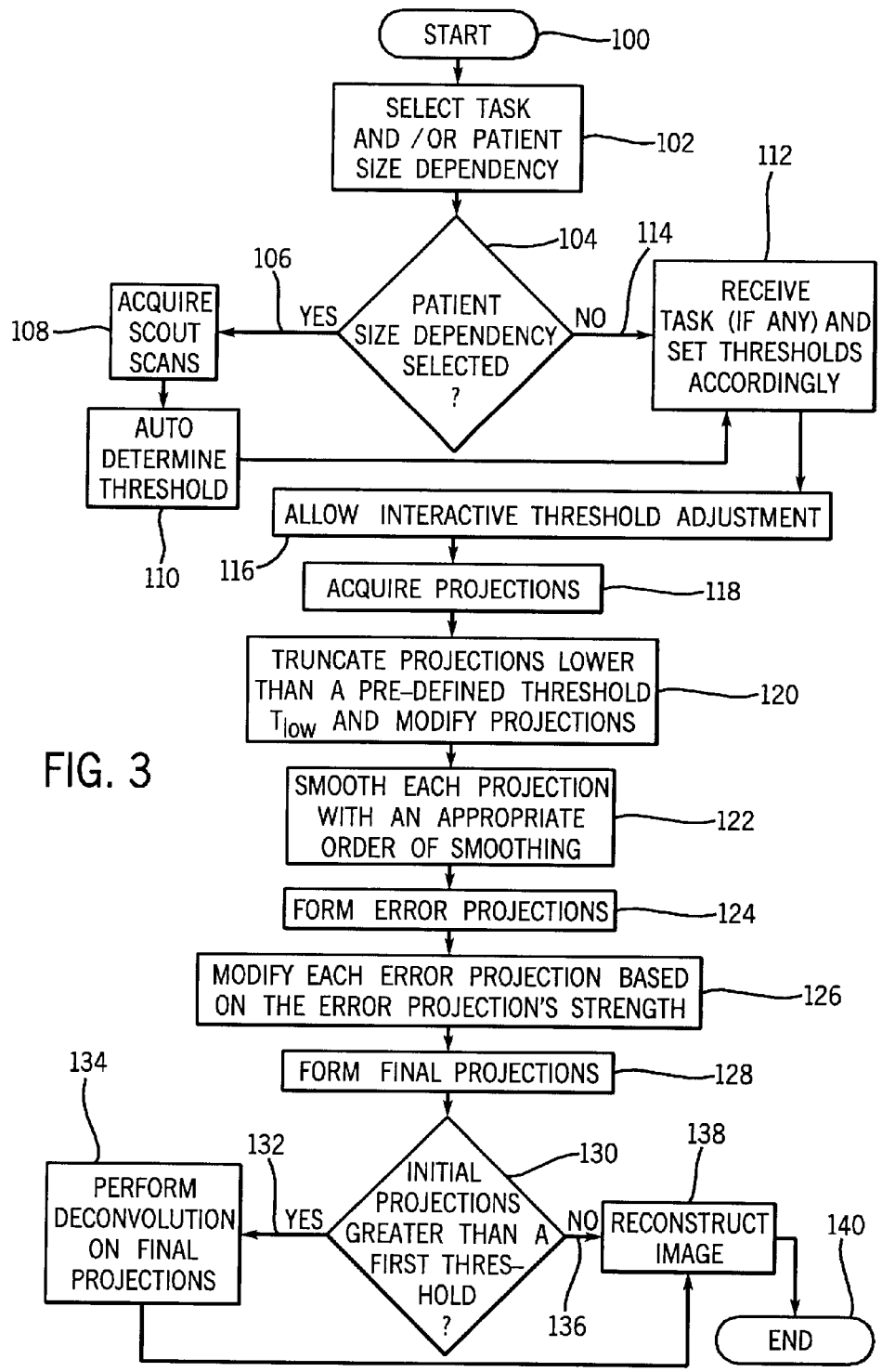
FIG. 3 is a flow chart showing a process of the present invention and implemented in the system of FIGS. 1 and 2.

Referring to FIG. 3, a flowchart illustrating the steps of a method and acts associated with a computer program in accordance with the present invention implemented in the system shown in FIGS. 1 and 2 are shown. The method and/or computer program is initiated at 100 by a technician or CT scanner operator who provides input into the computer at 102 to select a task and/or patient size dependency for a particular ROI. Generally, such operator-entered input can further include a starting position and an ending position along a common axis, such as axis 50 of FIG. 1 for conducting a scan. A patient size dependency query is then determined at 104, and if patient size dependency is selected 106, a scout scan is acquired 108. After acquiring the scout scan 108, the method and/or computer program proceeds to automatically determine a threshold at 110, and receive a task (if any) and set the thresholds accordingly 112. If patient size dependency is not selected 114, the method and/or computer program receives also receives a task (if any) at 112 and sets the thresholds accordingly. After thresholds are set 112, the method and/or computer program allows interactive threshold adjustment at 116 to change the threshold.

After allowing interactive threshold adjustment 112, initial projections are acquired 118 using projection techniques known to those skilled in the art. For example, in one embodiment using parallel projection CT scanners, a patient in a two dimensional plane (x, y) is irradiated by an X-ray source. Alternatively, other sources such as ultrasound and MRI may be used. The radiation emitted by the source penetrates the patient along straight lines in the two-dimensional plane and is attenuated as it passes through the patient. A detector measures such attenuated signals and calculates the projection measurement data as line integrals using the following equation:

$$P_n(j) = \int \int f(x,y) \partial(x \cos n_i + y \sin n_i - r_j) dx dy, \qquad (Eqn.\ 1)$$

wherein $P_n(j)$ are the calculated projections.

The acquired projections 118 that are lower than a defined threshold, $T_{low}$, are truncated to modify the projections 120. Preferably, the truncated projections are modified based on their initial values. The modified projections 120 are then smoothed 122. In one embodiment, the modified projections are grouped into first, second, and third projection sets having projection data above a first threshold, between the first and a second threshold, or below a third threshold respectively. Preferably, the first set of projections are smoothed using a lower order, 3-point smoothing technique, the second set of projections are smoothed using a medium order, 5-point smoothing technique, and the third set of projections are smoothed using a higher order, 7-point smoothing technique.

After smoothing the projections 122, error projections, $E_n(j)$ are formed 124 and modified based on each error projection's strength 126. In a preferred embodiment, the error projections are modified according to the following equations:

$$E_n(j) = P_n(j) - P_n(j)_{smoothed} \quad \text{(Eqn. 2)}$$

$$E_n(j)_{modified} = E_n(j) * M\_factor_n(j), \text{ and} \quad \text{(Eqn. 3)}$$

$$M\_factor_n(j) = \exp(-1.0 * P_n(j)/C\_factor), \quad \text{(Eqn. 4)}$$

wherein C_factor is a constant that depends on the threshold selections, $P_n(j)$ are the initial projections, $P_n(j)_{smoothed}$ are the smoothed projections, and $M\_factor_n(j)$ is the modification factor that modifies the error projections, $E_n(j)$ to form the modified error projections, $E_n(j)_{modified}$. After modification 126, the error projections are formed into a final set of projections 128.

The method next decides at 130 whether the initial projections are greater than a first threshold, and if so 132, performs Fourier deconvolution on the final set of projections 134. If the initial projections are not greater than the first threshold 136, an image is reconstructed 138. Similarly, the Fourier deconvoluted projections 134 are used to reconstruct an image at 138. The method then ends at 140.

As previously discussed and in accordance with one aspect of the present invention, a method of processing imaging data for a radiation emitting medical imaging device, such as a CT scanner, includes the steps of providing a task and patient size dependency selection and setting a first threshold level based on the task and patient size dependency selection. The method also includes the step of acquiring imaging data for image reconstruction, and separating the imaging data into a plurality of projections sets based on the first threshold level. The method further includes the step of uniquely processing the imaging data of each projection set prior to reconstruction of the image.

In accordance with another aspect of the invention, a computed tomography system is provided. This system includes a high frequency electromagnetic energy projection source to supply a patient dose or project high frequency energy towards a patient or object, and a detector to receive high frequency electromagnetic energy attenuated by the patient or object. The detector generates outputs that are transmitted to a data processing system by a plurality of electrical interconnects. The system also includes a computer programmed to receive the detector outputs, and a task and patient size selection input. The computer determines threshold levels based on the received task and patient size selection input, and is further programmed to separate the detector outputs into a plurality of projection sets based on the threshold levels. The computer is also programmed to reconstruct the separated plurality of projection sets, preferably after further image processing, and produce a visual image.

In accordance with yet another aspect of the invention, a computer-readable medium having stored thereon a computer program having a set of instructions that, when executed by a computer, will cause the computer to receive a selection signal of a task and patient size input and determine at least one threshold based upon the received selection signal. The computer program also includes instructions to receive imaging data signals acquired with low-dose radiation and synthesize the imaging data signals into a plurality of projection sets. The computer program further includes instructions to process each projection set based on the selection signal and the threshold to reconstruct a visual image.

The present invention has been described in terms of the preferred embodiment, and it is recognized that equivalents, alternatives, and modifications, aside from those expressly stated, are possible and within the scope of the append the steps ofing claims.

What is claimed is:

1. A method of processing imaging data for a radiation emitting medical imaging device, the method comprising the steps of:
   providing a task and patient size dependency selection;
   setting a first threshold level based on the task and patient size dependency selection;
   acquiring imaging data;
   separating the imaging data into a plurality of projection sets based on the first threshold level; and
   uniquely processing the imaging data of each projection set.

2. The method of claim 1 wherein the first threshold level is predetermined according to a selection of the task and patient size dependency selection.

3. The method of claim 2 further comprising the step of allowing interactive threshold adjustment.

4. The method of claim 1 wherein a patient size dependency is selected and the method further comprises acquiring a scout scan, and the step of setting a first threshold level includes automatically determining the first threshold level based on the scout scan.

5. The method of claim 4 further comprising the step of allowing interactive threshold adjustment.

6. The method of claim 1 wherein the step of providing a task and patient size dependency selection includes any of a selection of a task dependency, a patient size dependency, and a task and patient size dependency, and wherein the step of setting a first threshold level includes allowing interactive threshold adjustment by an operator.

7. The method of claim 1 further comprising the step of setting a second threshold level based on the task and patient size dependency selection, and wherein the imaging data is separated into three projection sets based on the first and second threshold levels.

8. The method of claim 7 wherein the unique processing of the imaging data of each projection set includes smoothing each of the three projection sets differently.

9. The method of claim 7 further comprising the step of performing Fourier deconvolution on the imaging data of the projection sets.

10. The method of claim 7 wherein a projection set having imaging values below the second threshold level is truncated.

11. The method of claim 10 wherein a truncated projection set, $P_{low}(j)$ is scaled according to: $P_n(j) = T_{low} * [1.0 + k * P_{low}(j)]$, where k is a constant, $T_{low}$ is the second threshold level, and $P_n(j)$ is an $n^{th}$ scaled projection of the truncated projection set.

12. A computed tomography system comprising:
   a high frequency electromagnetic energy projection source to project high frequency energy towards an object;
   a detector to receive high frequency electromagnetic energy attenuated by the object;
   a plurality of electrical interconnects configured to transmit detector outputs to a data processing system; and a computer programmed to:
  receive the detector outputs;
  receive a task and patient size selection input;
  determine threshold levels based on the task and patient size selection input;
  separate the detector outputs into a plurality of projection sets based on the threshold levels; and
  reconstruct the separated plurality of projection sets to produce a visual image.

13. The system of claim 12 wherein when a patient size is selected, the computer is further programmed to generate a scout scan and automatically determine a first threshold level based on the scout scan.

14. The system of claim 13 wherein the computer is further programmed to allow interactive threshold adjustment to reconfigure the visual image.

15. The system of claim 12 wherein the computer is further programmed to automatically determine a first threshold level based on the task and patient size selection input.

16. The system of claim 15 wherein the computer is further programmed to allow interactive threshold adjustment to modify the visual image and determine a second threshold level based on the task and patient size selection input.

17. The system of claim 16 wherein the computer is further programmed to truncate each projection set, $P_{low}(j)$, that contains data below the second threshold level, and wherein $P_{low}(j)$ is scaled according to: $P_n(j)=T_{low}*[1.0+k*P_{low}(j)]$, where k is a constant $T_{low}$ is the second threshold level, and $P_n(j)$ is an $n^{th}$ scaled projection of the truncated projection set.

18. The system of claim 12 wherein the computer is further programmed to Fourier deconvolute one or more of the plurality of projection sets.

19. The system of claim 12 wherein the computer is further programmed to smooth the plurality of projection sets.

20. The system of claim 19 wherein the plurality of projection sets is separated into three projection sets, and wherein each of the three projection sets is independently smoothed based on the threshold levels.

21. A computer-readable medium having stored thereon a computer program having a set of instructions that, when executed by a computer, causes the computer to:
  receive a selection signal of a task and patient size input;
  determine at least one threshold based upon the received selection signal;
  receive imaging data signals acquired with low-dose radiation;
  synthesize the imaging data signals into a plurality of projection sets; and
  process each projection set based on the selection signal and the threshold to reconstruct a visual image with improved artifact reduction.

22. The computer-readable medium of claim 21 wherein the determining of at least one threshold includes allowing interactive threshold adjustment by an operator after an automatic threshold selection.

23. The computer-readable medium of claim 21 wherein a first threshold level is determined according to selection signal indicative of a task, a patient size, or a task and patient size combination.

24. The computer-readable medium of claim 23 wherein the computer program causes the computer to permit interactive threshold adjustment.

25. The computer-readable medium of claim 21 wherein the selection signal is indicative of a patient size input and the computer is further programmed to receive scout scan data signals to reconstruct a scout scan image.

26. The computer-readable medium of claim 25 wherein a first threshold level is automatically determined based on the scout scan data signals.

27. The computer-readable medium of claim 21 wherein the computer program causes the computer to Fourier deconvolute the imaging data signals of the synthesized projection sets prior to image reconstruction.

28. The computer-readable medium of claim 21 wherein the computer program further causes the computer to:
  define first and second thresholds;
  generate a number of first projection sets having imaging data signals above the first threshold;
  generate a number of second projection sets having imaging data signals below the first threshold and above the second threshold; and
  generate a number of third projection sets having imaging data signals below the second threshold.

29. The computer-readable medium of claim 28 wherein the computer program stored thereon further causes the computer to uniquely smooth each of the number of first, second and third projection sets.

30. The computer readable medium of claim 28 wherein the computer program stored thereon further causes the computer to truncate the third projection sets wherein a truncated third projection set, $P_{low}(j)$ is scaled according to: $P_n(j)=T_{low}*[1.0+k*P_{low}(j)]$, where k is a constant, $T_{low}$ is the second threshold level, and $P_n(j)$ is an $n^{th}$ scaled projection of the truncated third projection set.

* * * * *